(12) United States Patent
Bowman

(10) Patent No.: US 9,170,378 B2
(45) Date of Patent: Oct. 27, 2015

(54) FIBER OPTIC ROTARY JOINTS, METHODS PRACTICED THEREBY, AND FIBER OPTIC DEVICES

(75) Inventor: Anthony L. Bowman, Ripplemead, VA (US)

(73) Assignee: Moog Inc., East Aurora, NY (US)

( * ) Notice: Subject to any disclaimer, the term of this patent is extended or adjusted under 35 U.S.C. 154(b) by 358 days.

(21) Appl. No.: 13/512,450

(22) PCT Filed: Dec. 3, 2009

(86) PCT No.: PCT/US2009/006350
§ 371 (c)(1),
(2), (4) Date: May 29, 2012

(87) PCT Pub. No.: WO2011/068492
PCT Pub. Date: Jun. 9, 2011

(65) Prior Publication Data
US 2012/0237198 A1   Sep. 20, 2012

(51) Int. Cl.
*G02B 6/36* (2006.01)
*G02B 6/42* (2006.01)
(Continued)

(52) U.S. Cl.
CPC ............ *G02B 6/3604* (2013.01); *G02B 6/4202* (2013.01); *H04B 10/225* (2013.01); *A61B 6/56* (2013.01)

(58) Field of Classification Search
CPC .................................................... G02B 6/3604
USPC ........................................................... 385/26
See application file for complete search history.

(56) References Cited

U.S. PATENT DOCUMENTS

| 4,436,367 A | 3/1984 | Lewis et al. |
| 4,525,025 A | 6/1985 | Hohmann et al. |

(Continued)

FOREIGN PATENT DOCUMENTS

| EP | 1583259 A2 | 10/2005 |
| JP | 2001519541 A | 10/2001 |

(Continued)

OTHER PUBLICATIONS

The International Search Report (ISR) and Written Opinion of the searching authority for PCT Application Serial No. PCT/US2009/006350; Publication No. WO 2011/068492 A1; dated Nov. 11, 2010.

(Continued)

*Primary Examiner* — Jerry Rahll
(74) *Attorney, Agent, or Firm* — Phillips Lytle LLP

(57) ABSTRACT

This invention provides a fiber optic rotary joint (20) for enabling the transmission of digital optical signals across the interface between facing surfaces (26, 29) of a rotor and a stator (21, 22), comprising: a plurality of light sources (42A, 42B, 42C, ...) mounted on one of the rotor and stator, each light source including a first light source (43C) arranged to selectively generate a first optical signal at a first wave length and a second light source (43C) arranged to selectively generate a second optical signal at a second wavelength; a first plurality of light emitters (25) spaced along a first arc distance of the surface of the one of the rotor and stator for transmitting optical signals received from the light sources toward the facing surface of the other of the rotor and stator; a first plurality of first optical fibers severally communicating respective ones of the light sources with respective ones of the light emitters for conveying optical signals from each respective light source to the associated emitter; a second plurality of light receptors (31) spaced along a second arc distance on the surface of the other of the rotor and stator; and at least one light detector (36, 40) mounted on the other of the rotor and stator; and a second plurality of second optical fibers severally communicating respective ones of the light receptors with the light detector(s).

24 Claims, 5 Drawing Sheets

(51) Int. Cl.
  *H04B 10/00* (2013.01)
  *A61B 6/00* (2006.01)

(56) References Cited

U.S. PATENT DOCUMENTS

| | | |
|---|---|---|
| 5,336,897 A | 8/1994 | Watanabe et al. |
| 5,991,478 A * | 11/1999 | Lewis et al. .................... 385/26 |
| 6,104,849 A | 8/2000 | Lewis et al. |
| 6,195,485 B1 | 2/2001 | Coldren et al. |
| 6,385,367 B1 | 5/2002 | Rogers et al. |
| 6,453,088 B1 | 9/2002 | Lewis et al. |
| 6,907,161 B2 | 6/2005 | Bowman |
| 6,980,714 B2 | 12/2005 | Lo et al. |
| 7,158,700 B2 | 1/2007 | Duncan et al. |
| 2005/0089272 A1 | 4/2005 | Tateiwa |
| 2005/0213972 A1 | 9/2005 | Aoki et al. |
| 2005/0254822 A1 | 11/2005 | Duncan et al. |
| 2006/0280216 A1 | 12/2006 | Jayaraman |

FOREIGN PATENT DOCUMENTS

| | | |
|---|---|---|
| JP | 2006278662 A | 10/2006 |
| JP | 2007187774 A | 7/2007 |
| JP | 2007292970 A | 11/2007 |
| WO | 2007130016 | 11/2007 |

OTHER PUBLICATIONS

The (IB/373) International Preliminary Report on Patentability Chapter I for International Patent Application No. PCT/US2009/006350; Publication No. WO 2011/068492 A1; dated Jun. 5, 2012.

* cited by examiner

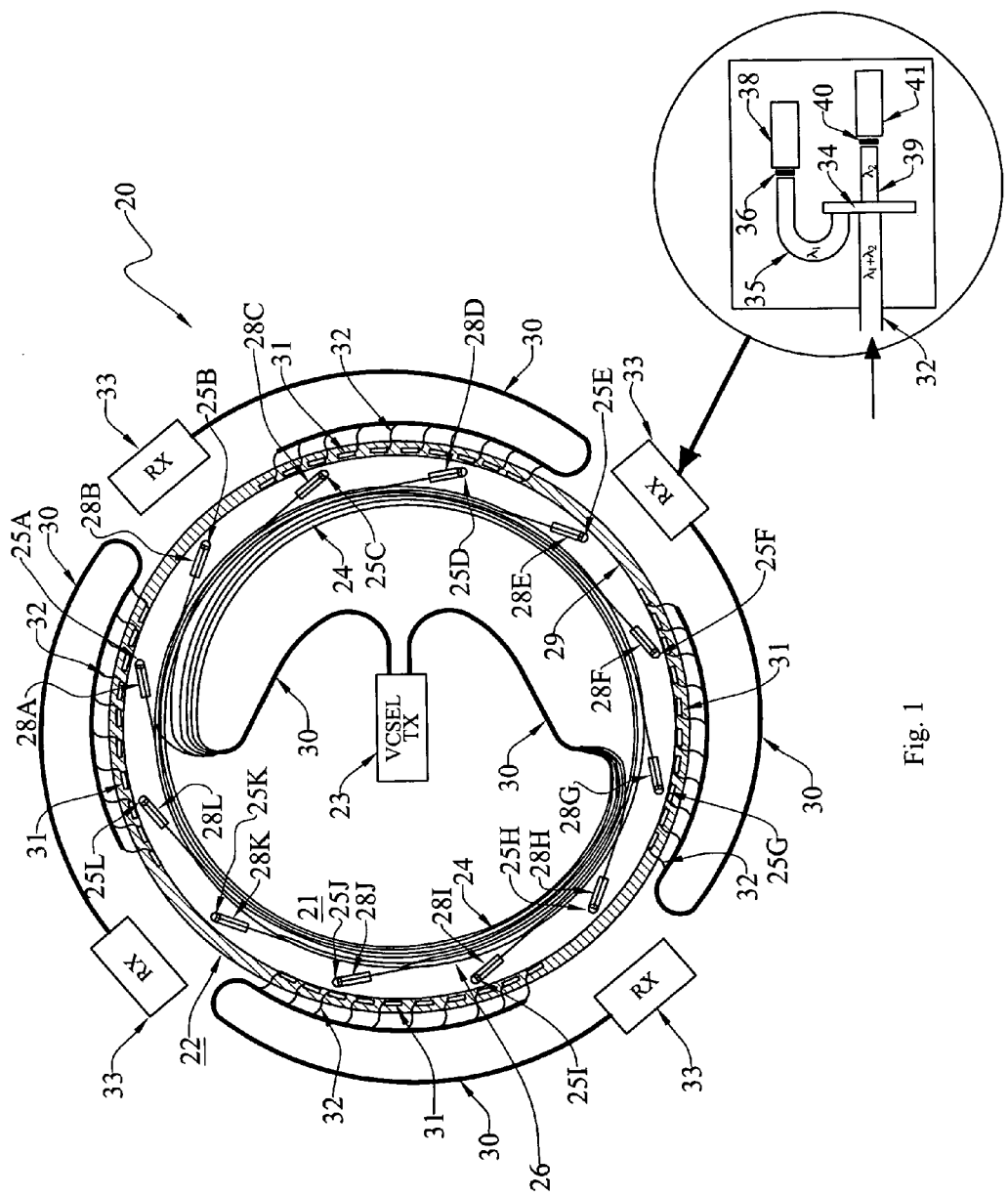

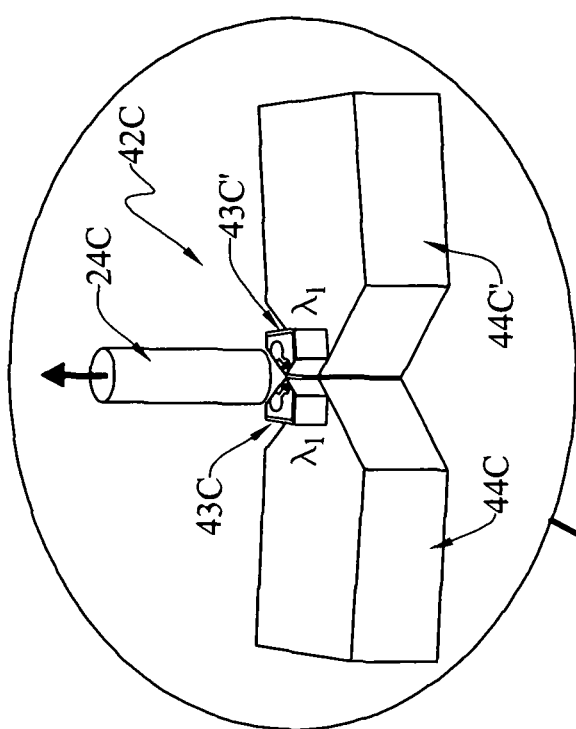
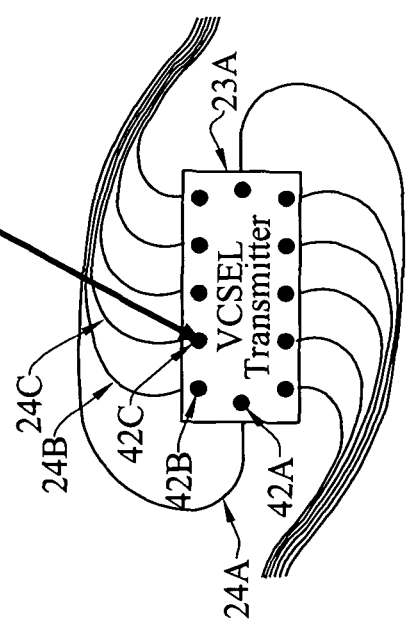
Fig. 2A
Fig. 2

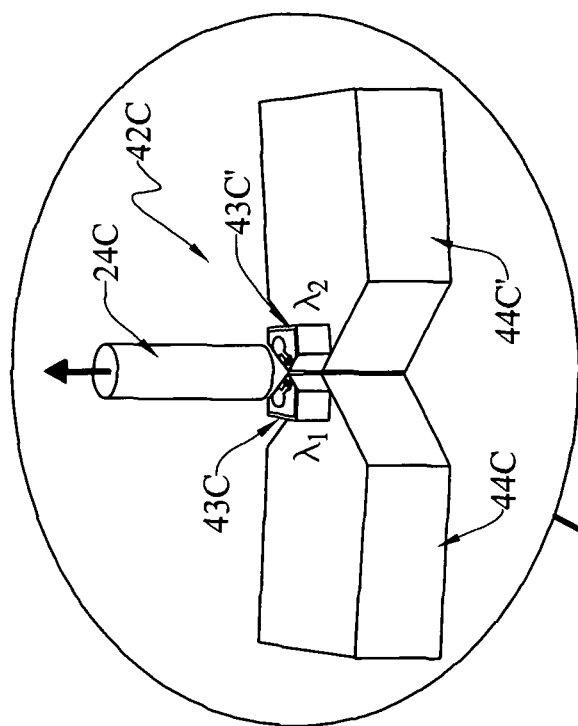
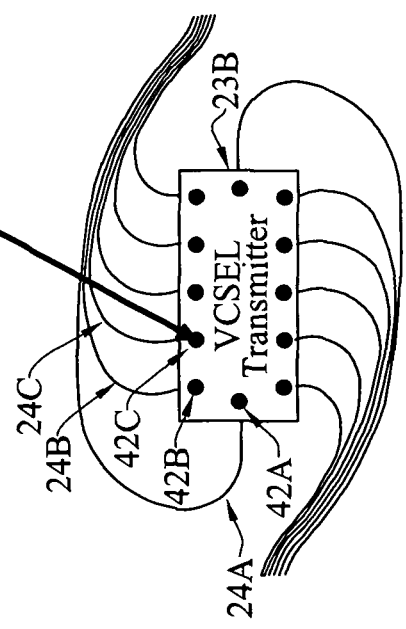
Fig. 3A
Fig. 3

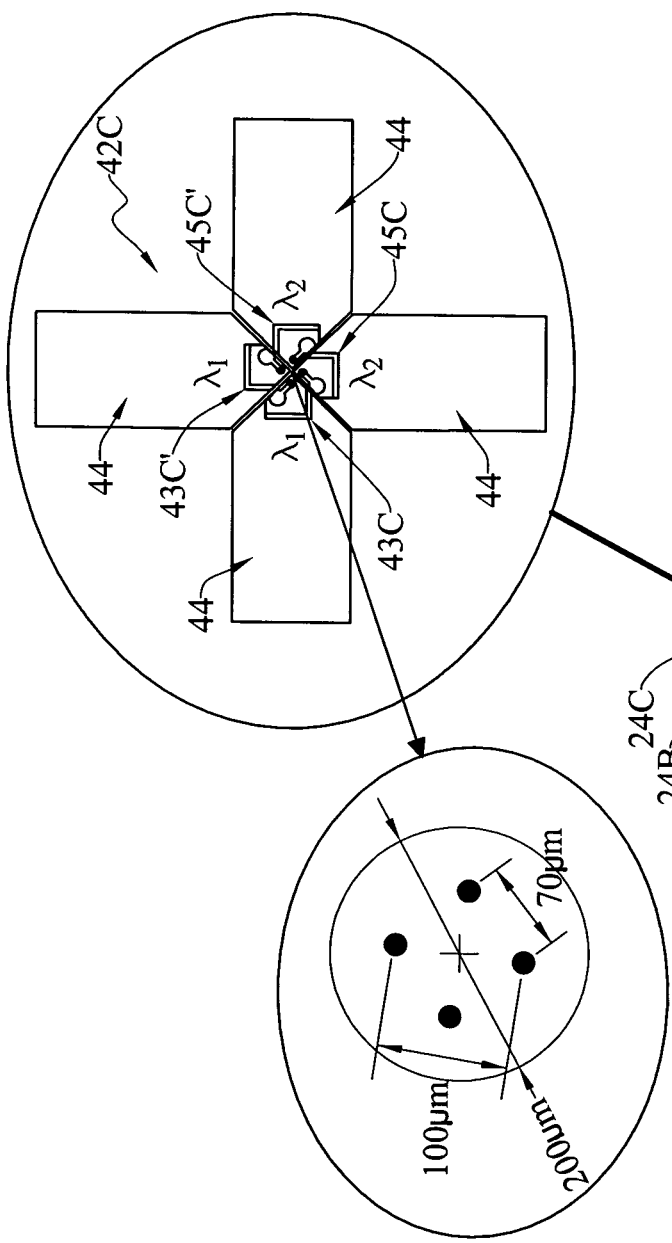
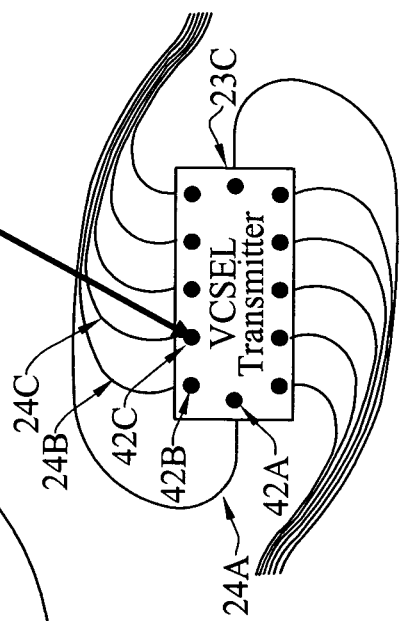
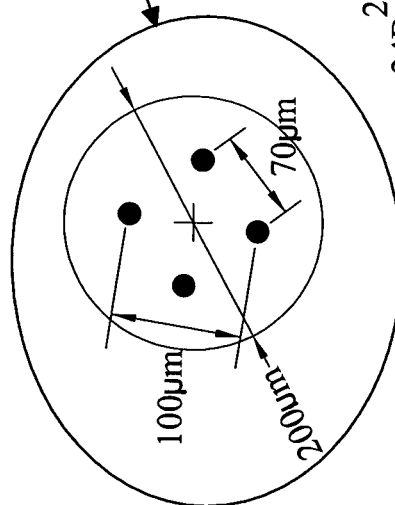
Fig. 4A
Fig. 4B
Fig. 4

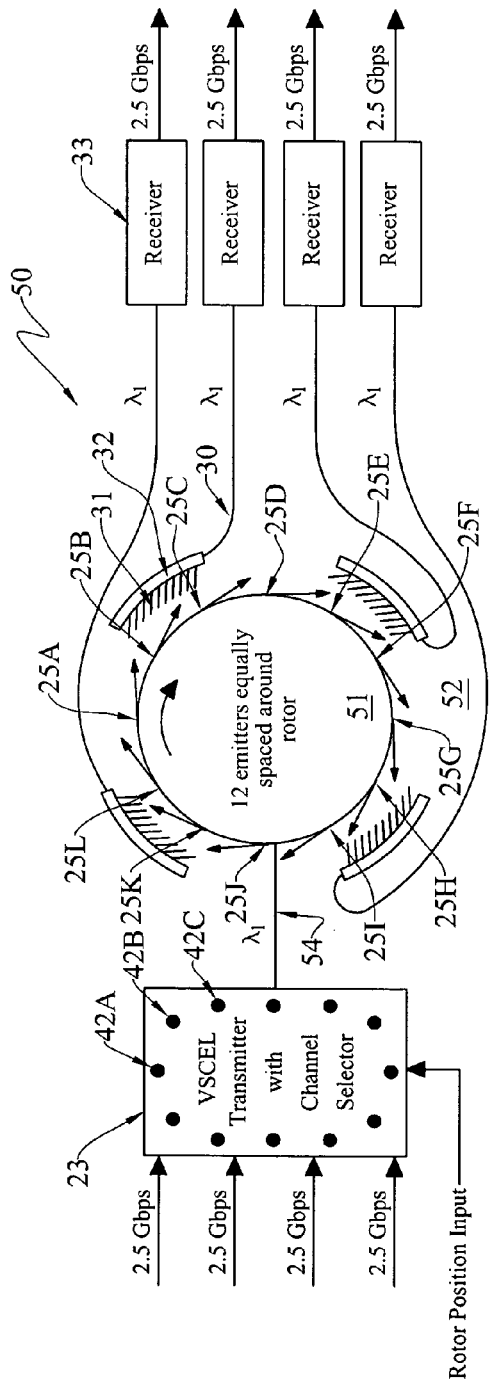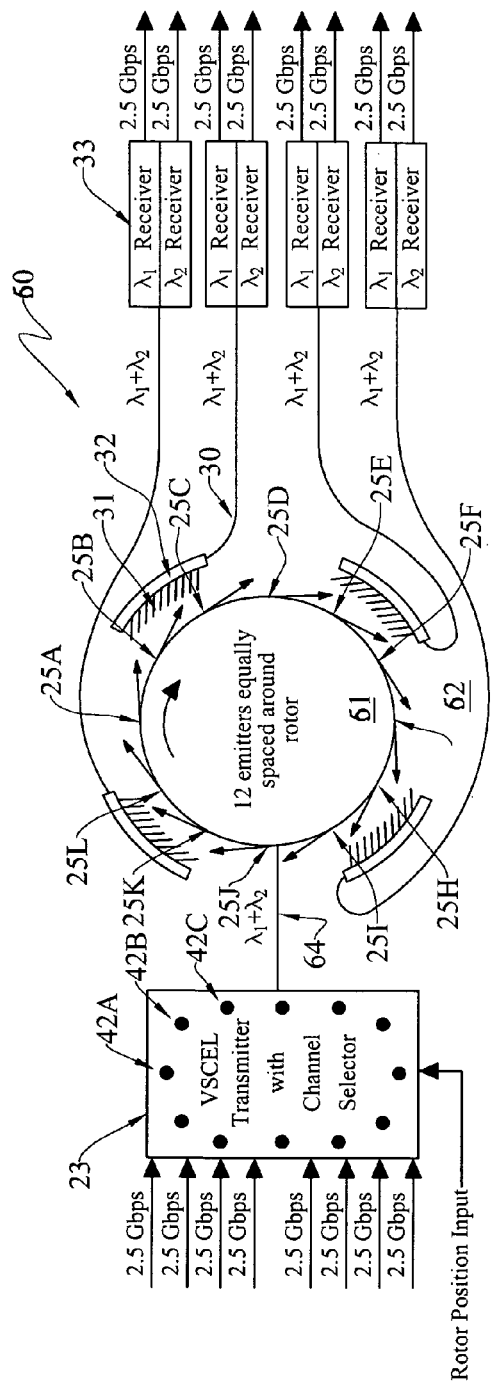

FIBER OPTIC ROTARY JOINTS, METHODS PRACTICED THEREBY, AND FIBER OPTIC DEVICES

TECHNICAL FIELD

The present invention relates generally to fiber optic rotary joints, and, more particularly, to improved compact lower-cost fiber optic rotary joints ("FORJs") that enable the transmission of high data rate (e.g., 2.5 Gbps or higher) digital optical signals across the interface between the facing peripheral surfaces of a rotor and a stator, to methods practiced thereby, and to improved fiber optic devices.

BACKGROUND ART

Fiber optic rotary joints exist in a myriad of different forms and structures. In many cases, such joints have a rotor mounted for rotational movement relative to a stator. One or more optical signals can be transmitted across the interface between the rotor and stator (i.e., from the rotor to the stator and/or vice versa).

Contactless off-axis fiber optic rotary joints have been developed, such as disclosed in U.S. Pat. No. 4,525,025 A, which is assigned to the assignee of the present invention. The '025 patent discloses a fiber optic rotary joint that transmits a pulsed optical signal across a rotary interface. This device includes an annular reflective wall formed on a stator, and an optical fiber also mounted on the stator and having one end arranged tangentially proximate the annular reflective wall. A signal emitted by one of a plurality of rotor-mounted optical fibers will be transmitted across the annular interface between the rotor and stator, will be reflected along the annular reflective wall, and will be received by a respective one of the stator-mounted optical fibers.

Actual joints constructed in a manner generally similar to that disclosed in the '025 patent have been limited to rotor diameters of about ten to twelve inches, and data transmission rates of 50 megabits/sec ("Mbps"), due to various propagation delays that cause bit pulse-width distortion. There is a need for joints having rotor diameters of 101.6-127.0 centimeters [i.e., 40-50 inches] using pulsed optical signals having data transfer rates of 1-3 gigabits/sec ("Gbps") or more. To meet these requirements, two criteria must be met. First, optical variations with rotation must be minimized. Second, propagation delays must be controlled to minimize their effect on bit pulse-width distortion.

U.S. Pat. No. 5,336,897 A discloses an optical data transmission apparatus which is used to transmit a signal between the rotating and fixed portions of an X-ray CT scanner. The apparatus includes light-emitting elements arranged on a side plane of the rotating portion, which side plane is perpendicular to the rotational axis of such portion. The light-emitting elements are uniformly driven according to transmission data to emit lights in a direction parallel to the rotational axis. A light-receiving element is disposed on the side plane of the fixed portion which faces the light-emitting elements. The interval between the light-emitting elements is set so that the illumination areas formed by the various light-emitting elements partly overlap each other on the light-receiving element. Therefore, the light-receiving element always receives light from one or two of the light-emitting elements. During rotation of the rotating portion, data can be continuously transmitted from all of the light-emitting elements to the various light-receiving elements.

U.S. Pat. No. 5,991,478 A and U.S. Pat. No. 6,104,849 A disclose FORJs having a waveguide on the stator. Unidirectional and bidirectional FORJs are disclosed for transmitting at least one optical signal across a rotary interface. The FORJs include a stator having a waveguide. The rotor is rotatable through 360°, and is concentric with the stator. Light transmitters are positioned on a first circumference on one of the stator and rotor. Each of the transmitters emits an optical signal. Light receivers are positioned on a second circumference of the other of the rotor and stator. Each of the transmitted optical signals is emitted tangentially into the waveguide, and is reflected in short chordal lengths therealong. Each optical signal is received by at least one of the second plurality of light receivers at any relative angular position between the rotor and the stator. The number of light receivers is greater than the number of light transmitters. Certain receivers do not receive an optical signal during a portion of the 360° revolution of the rotor.

U.S. Pat. No. 6,385,367 B1 discloses FORJs comprised of multiple segmented circumferentially-spaced waveguides located on the stator. Spaces between the waveguides are non-reflective. Each waveguide has an optical pickup. A plurality of optical transmitters are located on the rotor. In the preferred embodiment, there are sixteen transmitters, with eight transmitters transmitting at any given time and eight transmitters turned off at that same time. This reference also teaches the use of a switch for routing each input data stream to the appropriate transmitter that transmits a corresponding optical signal to a predetermined waveguide segment for that particular angular position of the rotor relative to the stator such that each transmitter will transmit an individual optical signal to its associated waveguide at that particular angular position.

U.S. Pat. No. 6,453,088 B1 discloses segmented waveguides for large-diameter FORJs. The waveguides are mounted to the existing stator surface. Each waveguide is capable of receiving signals from the rotor. The FORJ includes a rotor and an existing stator surface. The rotor is rotatable through 360°, and is concentric with the existing stator surface. The rotor has one of a plurality of light transmitters and light receivers connected to a first circumference of the rotor. The waveguides include a reflective waveguide surface shaped to match a portion of the existing stator surface. At least one waveguide support holds the reflective waveguide surface and is connected to the existing stator. At least one of a light transmitter or light receiver is optically coupled to a reflective waveguide surface.

U.S. Pat. No. 6,907,161 B2 discloses FORJs that eliminate the lens/prism assemblies and the multiple pick-up fibers that must be multiply-lensed to a detector to get sufficient signal strength for the system to work. The FORJ also compensates for some of the rapid rise and fall time of certain system components. A single pick-up, either a fiber or a photodiode, is placed at the end of a waveguide. A lens or lens system is used to focus a single optical signal onto the fiber face or the photodiode active area. Various light injection techniques, such as fibers, fiber/lens assemblies, lensed VCELs, lasers, LEDs and the like, can be utilized because of the location in the system.

U.S. Pat. No. 6,980,714 B2 discloses FORJs and associated reflector assemblies for supporting optical communications between a rotor and a stator. The FORJs include at least one optical source carried by the rotor or the stator for transmitting optical signals. The FORJ also includes a reflector mounted on the other of the rotor and stator for reflecting the optical signals, and a receiver for receiving the optical signals following their reflection. The reflector is generally shaped and positioned such that the path lengths along which the optical signals propagate from the optical source(s) to the receivers are equal, regardless of the rotational position of the rotor relative to the stator. The reflector may have a reflective surface shaped to define a portion of an ellipse and/or a reflective surface shaped to define a portion of a hyperbola.

International Pub. No. WO 2007/130016 A1 discloses optical rotary joints for enabling optical communication between a rotor and a stator, improved methods of mounting such optical rotary joints on supporting structures such that the rotor and stator remain properly aligned, and improved optical reflector assemblies for use in such optical rotary joints. The improved optical rotary joints enable optical communication between a rotor and a stator. The rotor has a longitudinal axis, and includes at least one optical source mounted on one of said rotor and stator for transmitting an optical signal in a radial direction with respect to the longitudinal axis, and at least one first reflector mounted on the other of the rotor and stator for reflecting the optical signal transmitted from the source. The first reflector includes a concave first reflective surface. A line in a plane taken through the first reflective surface is configured as a portion of an ellipse having first and second focal points. The first focal point is positioned substantially coincident with the rotor axis. A second reflector, having a second reflective surface configured as a portion of a cone, is positioned at the second focal point of the elliptical surface for receiving light reflected from the first reflective surface, and reflects light in a different direction as a function of the apex angle of the second reflective surface. A receiver is arranged to receive light reflected by the second reflective surface.

Finally, U.S. Pat. No. 7,158,700 B2 discloses fiber-optic transceivers in which a light source and a photodiode are arranged in aligned spaced relation to the proximal end of an optical fiber. The light source is arranged to emit light into the fiber, and the photodiode is arranged to receive light from the fiber.

In CT scanner applications, in which the axis of rotation of a rotor is sometimes physically occupied by a patient, off-axis rotary joints are generally employed to transmit signals between the rotor and stator. Such off-axis rotary joints generally include one or more light sources for emitting optical signals, and arcuate reflectors having channel-shaped transverse cross-sections that receive such transmitted signals and direct such received signals to respective light receivers. The optical sources are spaced circumferentially about one of the rotor and stator, while the reflectors and receivers are spaced circumferentially about the other of the rotor and stator. The optical sources may include one or more common light sources. The optical signals from these light sources may be directed, as by optical fibers, to the periphery of the associated one of the rotor and stator. Alternatively, the optical sources may be separate emitting elements mounted about such periphery. For example, the optical sources may be disposed circumferentially about the rotor, while the multiple reflectors and receivers may be disposed circumferentially about the stator, thereby supporting optical communications from the rotor to the stator. In most cases, the path of optical data transmission across the rotary joint (i.e., between the rotor and stator) is in a radial direction with respect to the rotor axis. In other words, if light is transmitted from the rotor to the stator, the light is seen as coming from the rotor axis, regardless of the physical location of the light source(s).

In operation, each of the light sources may possibly transmit the same optical signal. These signals may be transmitted across the rotary interface, and may be received by one or more of the reflectors and be directed to the associated receivers, depending upon the angular position of the rotor relative to the stator. In other embodiments, different optical signals may be transmitted from different light sources, or may be multiplexed if coming from the same source.

While generally effective for permitting optical communication between a rotor and a stator, some conventional off-axis rotary joints that employ such arcuate reflectors with channel-shaped cross-sections suffer from certain shortcomings, especially at higher data transmission rates. These problems may include: (a) the broadening of superimposed pulse widths due to different-length light transmission paths, and (b) a greater number of light sources must be used when transmitting signals into the entrance end of an optical fiber than when such signals are incident directly upon a photodetector, as discussed infra. In addition, some signal collection arrangements may have variable optical path lengths that practically limit the design to data transmission rates of about 2.5 Gbps.

For example, in conventional off-axis rotary joints, the optical signals may travel along different-length paths between the various sources and the respective receivers, thereby introducing time delays in the various received optical signals, when superimposed. A particular receiver might receive signals from two circumferentially-adjacent optical sources. If the same optical signal is simultaneously emitted by the two adjacent sources, but such signals travel different distances to reach the receiver, the signals will be received at different times. Accordingly, the two signals will be out-of-phase, and the pulse width of the superimposed signals, as seen by the receiver, will be effectively broadened. To support communication at the desired high data rates, conventional off-axis rotary joints have been specifically designed to have less spacing between the optical sources and the receivers so as to minimize the path lengths of signal travel. Even so, it is difficult to support error-free data transmission at a data rate above 1.25 Gbps, where the signals travel along different-length paths.

The aggregate disclosures of each of the foregoing patents are hereby incorporated by reference.

Accordingly, it would be generally desirable to provide improved low-cost FORJs that are capable of high data rate transmission.

DISCLOSURE OF THE INVENTION

The present invention broadly provides improved lower-cost FORJs with reduced path length variations for enabling the transmission of one or more digital optical signals across the interface between the facing peripheral surfaces of a rotor and a stator, to improved methods practiced thereby, and to improved optical fiber devices.

In one aspect, the invention provides a fiber optic rotary joint (20) for enabling the transmission of a digital optical signal across the interface between facing surfaces (26, 29) of a rotor (21) and a stator (22), which broadly includes: a plurality of light sources (42A, 42B, 42C, . . . ) mounted on one of the rotor and stator, each light source including a first light source (43C) arranged to selectively generate an optical signal and a second light source (43C') arranged to selectively generate the same optical signal; a first plurality of light emitters (25A, 25B, 25C, . . . ) spaced equidistantly along the surface of the one of the rotor and stator and separated individually by a first arc distance for transmitting the optical signal received from the light sources toward the facing surface of the other of the rotor and stator; a first plurality of first optical fibers (24A, 24B, 24C, . . . ) severally communicating respective ones of the light sources with respective ones of the light emitters for conveying the optical signal from each respective light source to the associated emitter; a second plurality of light receptors (31) spaced equidistantly along the surface of the other of the rotor and stator and separated individually by a second arc distance; at least one light detector (36, 40) mounted on the other of the rotor and stator; and a second plurality of second optical fibers (32) severally communicating respective ones of the light receptors with the light detector(s). The light sources, first optical fibers, light emitters, light receptors, second optical fibers and detector(s) are so configured and arranged that the aggregate propagation delay of the optical signal transmitted from the light sources to the detector(s) is less than about one-quarter of the bit width of the optical signal. The improved fiber optic rotary joint is, therefore, capable of transmitting the optical signal across the interface with reduced jitter.

The first light source (43C) is arranged to normally generate the optical signal. The second light source (43C') is arranged to generate the optical signal if the first light source fails to generate the optical signal.

The fiber optic rotary joint may further include: a sensor for sensing whether the first light source is generating the optical signal; and a switch arranged to cause the second light source to generate the optical signal if the first light source fails to generate the optical signal. The switch may operate automatically upon the sensed absence of the optical signal generated by the first light source, or the sensed absence of power drawn by the first light source. However, the coupling of the optical signal to the associated first optical fiber remains substantially uninterrupted.

The optical signal transmitted across the interface may have a data transmission rate of at least about 2.5 Gbps.

The first and second arc distances may be subtended by different angles. In one form, the light emitters are separated by an interval of about 30° and the second arc distance is about 36°.

The first optical fibers may be of substantially equal lengths. The second optical fibers (32) may be of substantially equal lengths. The core of each first optical fiber and/or the core of each second optical fiber may have a diameter of at least about 200 microns. The core of each of the fibers may be glass.

The first plurality of first optical fibers may be different from the second plurality of second optical fibers. The first and second optical fibers may be of different lengths.

Each of the first optical fibers may have a collimating lens assembly (28A, 28B, 28C, . . . ) at a marginal end portion remote from its associated light sources. Each of the second optical fibers may have a collimating lens assembly at a marginal end portion remote from the light detector(s).

The signal-to-be-transmitted may be coupled into various of the first optical fibers prior to transmission across the interface, optically multiplexed, and transmitted by the plurality of light emitters across the interface. Such transmitted signals may be received by the second optical fibers, and such received signals may be optically demultiplexed to reform the signal-to-be-transmitted.

A number of the second plurality of light receptors may be spaced about the surface of the other of the rotor and stator.

In another aspect, the invention provides an improved fiber optic rotary joint (20) for enabling the transmission of digital optical signals across the interface between facing surfaces (26, 29) of a rotor (21) and a stator (22). The improved fiber optic rotary joint broadly includes: a plurality of light sources (42A, 42B, 42C, . . . ) mounted on one of the rotor and stator, each light source including a first light source (43C) arranged to selectively generate a first optical signal at a first wavelength ($\lambda_1$) and a second light source (43C') arranged to selectively generate a second optical signal at a second wavelength ($\lambda_2$); a first plurality of light emitters spaced equidistantly along the surface of the one of the rotor and stator and separated individually by a first arc distance for transmitting the optical signals received from the light sources toward the facing surface of the other of the rotor and stator; a first plurality of first optical fibers (24A, 24B, 24C, . . . ) severally communicating respective ones of the light sources with respective ones of the light emitters for conveying the optical signals from each respective light source to the associated emitter; a second plurality of light receptors (31) spaced equidistantly along the surface of the other of the rotor and stator and separated individually by a second arc distance; at least one light detector (36, 40) mounted on the other of the rotor and stator; and a second plurality of second optical fibers (32) severally communicating respective ones of the light receptors with the light detector(s). The light sources, first optical fibers, light emitters, light receptors, second optical fibers and detector(s) are so configured and arranged that the aggregate propagation delay of the optical signals transmitted from the light sources to the detector(s) is less than about one-quarter of the bit width of the optical signals. The improved fiber optic rotary joint is, therefore, capable of transmitting the optical signals across the interface with reduced jitter.

Each light source may include two of the first light sources (43C, 43C') severally arranged to selectively generate the first optical signal, and two of the second light sources (45C, 45C') severally arranged to selectively generate the second optical signal.

One of the first light sources (43C) is arranged to normally generate the first optical signal, and the other of the first light sources (43C') is arranged to generate the first optical signal if the one first light source does not generate the first optical signal. One of the second light sources (45C') may be arranged to normally generate the second optical signal if the second light source (45C) does not generate the second optical signal.

The fiber optic rotary joint may further include: a position determining device for determining the relative angular position between the rotor and stator; means for supplying a plurality of individual input data streams to the joint; and a switch (23) for routing each individual input data stream to a respective one of the light sources that communicates with the appropriate emitter that is arranged to transmit a corresponding optical signal to a predetermined light receptor for that particular relative angular position between the rotor and stator such that each light emitter will transmit an individual optical data signal to such associated light receptor at such relative angular position so that the individual input data streams will be transmitted continuously to respective ones of the light receptors at any relative angular position between the rotor and the stator.

In another aspect, the invention provides an improved method of enabling the transmission of a digital optical signal across the interface between facing surfaces (26, 29) of a rotor (21) and a stator (22), which includes the steps of: providing a plurality of light sources (42A, 42B, 42C, . . . ) on one of the rotor and stator, each light source including a first light source (43C) arranged to selectively generate an optical signal and a second light source (43C') arranged to selectively generate the optical signal; providing a first plurality of spaced light emitters spaced equidistantly along the surface of the one of the rotor and stator and separated individually by a first arc distance; providing a first plurality of first optical fibers between respective ones of the light sources and respective ones of the light emitters; causing the light sources to emit the optical signal; conveying the optical signal from the light sources to the light emitters along the first optical fibers; causing the first light emitters to transmit the optical signal across the interface toward the facing surface of the other of the rotor and stator; providing a second plurality of spaced light receptors (31) spaced equidistantly the surface of the other of the rotor and stator and separated individually by a second arc distance for receiving the optical signals transmitted by the light emitters; providing at least one light detector (36, 40) on the other of the rotor and stator; conducting the optical signal received by the light receptors to the light detector(s); and positioning the light emitters and light receptors such that the aggregate propagation delay of the optical signal transmitted between the sources and detector(s) is less than about one-quarter of the bit width of the optical signal; thereby to enable the transmission of the digital optical signals across the interface with reduced jitter.

The first light source may be normally arranged to generate the optical signal.

The improved method may further include the additional steps of: sensing whether the first light source (43C) generates the optical signal; and causing the second light source (43C') to generate the optical signal if the first light source fails to generate the optical signal.

The improved method may further include the additional steps of: coupling the signal-to-be-transmitted into each of the first optical fibers prior to transmission across the interface; multiplexing the signal-to-be-transmitted; transmitting the signal by the plurality of light emitters across the interface; receiving such transmitted signal by the second optical fibers; and demultiplexing the transmitted signal to reform the signal-to-be-transmitted.

In another aspect, the invention provides an improved method of enabling the transmission of digital optical signals across the interface between facing surfaces (26, 29) of a rotor and a stator, which includes the steps of: providing a plurality of light sources on one of the rotor (21) and stator (22), each light source including a first light source arranged to selectively generate a first optical signal at a first wavelength ($\lambda_1$) and a second light source arranged to selectively generate a second optical signal at a second wavelength ($\lambda_2$); providing a first plurality of light emitters (42A, 42B, 42C, ...) spaced equidistantly along the surface of the one of the rotor and stator and separated individually by a first arc distance; providing a first plurality of first optical fibers between respective ones of the light sources and respective ones of the light emitters; causing the light sources to emit the optical signals; conveying the optical signals from the light sources to the light emitters along the first optical fibers; causing the first light emitters to transmit the optical signal across the interface toward the facing surface of the other of the rotor and stator; providing a second plurality of light receptors (31) spaced equidistantly along the surface of the other of the rotor and stator and separated individually by a second arc distance for receiving the optical signals transmitted by the light emitters; providing at least one light detector (36, 40) on the other of the rotor and stator; conducting the optical signals received by the light receptors to the light detector(s); and positioning the light emitters and light receptors such that the aggregate propagation delay of the optical signal transmitted between the sources and detector(s) is less than about one-quarter of the bit width of the optical signal; thereby to enable the transmission of the digital optical signals across the interface with reduced jitter.

This method may include the additional steps of: supplying a plurality of individual input data streams to the joint; determining the relative angular position between the rotor and stator; routing each input data stream to the appropriate emitter that transmits a corresponding optical signal to a predetermined light receptor for that determined relative angular position such that each light emitter will transmit an individual optical data signal to such associated light receptor at such relative angular position; and continuously transmitting each of the individual optical data signals to respective ones of the light receptors at any relative angular position of the rotor and stator.

In another aspect, the invention provides a fiber optic transmitter (42A) adapted to transmit optical signals into a fiber optic network, which includes: an optical fiber (24C) having a proximal end; and a plurality of light sources (43A) operatively arranged to selectively emit light energy into the fiber through the proximal end.

Each of the light sources may be a VCSEL transmitter.

The fiber may be a multi-mode fiber, and may have a core diameter of at least about 200 microns.

The fiber optic network may be a fiber optic rotary joint (20).

The fiber optic transmitter may be part of a fiber optic transceiver.

The plurality may be two.

Each of the light sources may be arranged to selectively generate the same optical signal, one of the light sources is arranged to normally generate the optical signal, and the other of the light sources is arranged to generate the optical signal if the first source fails to generate the optical signal.

The improved transmitter may further include: a sensor for sensing whether the first light source is generating the optical signal; and a switch arranged to cause the second light source to generate the optical signal if the first light source fails to generate the optical signal.

The light sources may be operatively arranged to selectively emit light energy at different wavelengths ($\lambda_1, \lambda_2$) into the fiber through the proximal end.

The plurality may be four.

Each light source of a first pair of the light sources may be arranged to selectively emit light energy at a first wavelength ($\lambda_1$), and each light source of a second pair of the light sources may be arranged to selectively emit light energy at a second wavelength ($\lambda_2$).

One of the light sources (43C) in one of the pairs may be arranged to normally emit the light energy, and the other of the light sources (43C') of such one pair may be arranged to emit light energy if the one light source of such pair fails to emit the light energy.

Each of the light sources may be a VCSEL transmitter. The VCSEL transmitters may be arranged at the corners of an imaginary rectangle, and wherein the centerline spacing between adjacent transmitters is about 68-72 microns.

Accordingly, the general object of the invention is to provide improved FORJs for enabling the transmission of digital optical signals across the interface between the facing peripheral surfaces of a rotor and stator.

Another object is to provide improved FORJs having low-cost rotor and stator topology with redundant light sources at the same wavelength such that if one fails, the other will continue.

Another object is to provide improved FORJs having low-const rotor and stator topology with redundant light sources at each of two separate wavelengths.

Another object is to provide improved methods for enabling the transmission of digital optical signals across the interface between the facing surfaces of a rotor and stator.

Still another object is to provide improved fiber optic devices.

These and other objects and advantages will become apparent from the foregoing and ongoing written specification, the drawings and the appended claims.

BRIEF DESCRIPTION OF THE DRAWINGS

FIG. 1 is a schematic view of an improved fiber optic rotary joint having twelve rotor-mounted light emitters operatively arranged to transmit optical signals across a rotary interface to ten receptors in each quadrant of the stator, and then via bundled fibers to system receivers, this arrangement being suitable for transmitting a 20 Gbps signal with wave division multiplexing.

FIG. 1A is an enlarged schematic view of one of the receivers, showing the use of a dichroic filter to separate the two received optical signals.

FIG. 2 is a top plan view of a first VCSEL transmitter with various light sources and twelve connected optical fibers.

FIG. 2A is an enlarged fragmentary perspective schematic view of two same-wavelength light sources ($\lambda_1$-$\lambda_1$) operatively arranged to supply an optical signal into the entrance end of an optical fiber.

FIG. 3 is a top plan view of a second VCSEL transmitter with various light sources and twelve connected optical fibers.

FIG. 3A is an enlarged perspective schematic view of two different wavelength light sources ($\lambda_1$-$\lambda_2$) operatively arranged to couple two different optical signals into the entrance end of an optical fiber.

FIG. 4 is a top plan view of a third VCSEL transmitter with various light sources and twelve connected optical fibers.

FIG. 4A is an enlarged top plan view of two same-wavelength first light sources ($\lambda_1$-$\lambda_1$) and two different-wavelength second light sources ($\lambda_2$-$\lambda_2$) operatively arranged to couple two different redundant optical signals into the entrance end of an optical fiber.

FIG. 4B is an enlarged schematic showing the spacing of the VCSEL transmitters shown in FIG. 4A, and the diameter of a 200 micron glass fiber core.

FIG. 5 is a schematic view of an improved FORJ that is supplied with four 2.5 Gbps electrical signals, that selectively generates single-wavelength individual optical data signals, and that selectively switches such individual optical data signals among the various rotor-mounted emitters such that the individual optical data signals will be transmitted continuously to respective ones of the light receptors at any relative angular position between the rotor and stator.

FIG. 6 is a schematic view of an improved FORJ that is supplied with eight 2.5 Gbps electrical signals, that selectively generates multiple-wavelength individual optical data signals, that selectively switches such individual optical data signals among the various rotor-mounted emitters such that the individual optical data signals will be transmitted continuously to respective ones of the light receptors at any relative angular position between the rotor and stator, and that subsequently separates the received signals.

DESCRIPTION OF PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, the present invention broadly provides improved fiber optic rotary joints for enabling the transmission of digital optical signals across the interface between facing surfaces of a rotor and stator, to improved methods of enabling the transmission of digital optical signals across such interface, and to improved fiber optic devices.

As best shown in FIG. 1, a first form of the improved fiber optic rotary joint is generally indicated at 20. This device has a rotor 21 mounted for rotational movement within a stator 22. A VCSEL light transmitter 23 is shown as being centrally mounted on the rotor. A first plurality of first optical fibers, severally indicated at 24, communicate the various light sources on the transmitter, as discussed infra, with respective ones of a first plurality of light emitters 25 spaced equidistantly along the surface of the rotor and separated individually by a first arc distance. There are twelve light emitters spaced equidistantly about the outwardly-facing surface 26 of the rotor, as shown in FIGS. 2-4. The various light emitters are severally indicated at 25, and are individually identified by the letters A, B, C, . . . , L. These various emitters, 25A, 25B, 25C, . . . , 25L, are operatively arranged to emit light through collimators 28A, 28B, 28C, . . . , 28L, respectively, across the rotary interface between rotor surface 26 and inwardly-facing stator surface 29. The various first optical fibers are of equal length, and are shown as being bundled, as indicated at 30, in the vicinity of the VCSEL transmitter.

The stator is shown as having a plurality of light receptors arranged in each of its four quadrants. There are ten light receptors, severally indicated at 31, in each quadrant, and these are connected via second optical fibers, severally indicated at 32, to four light receivers, severally indicated at 33. In the illustrated form, the ten light receptors in each quadrant occupy an arc distance of about 36°. The second fibers are shown as being bundled, as again indicated at 30, in the vicinity of the receiver.

In the illustrated form, the facing surfaces of the rotor and stator are shown as being annular. However, this need not invariably obtain.

Referring now to FIG. 1A, each receiver 33 is shown as being connected to each of the fibers 32 in a quadrant. These fibers may contain a single optical signal (i.e., $\lambda_1$) or may contain more than one signal (i.e., $\lambda_1$+$\lambda_2$), as appropriate. In either event, the signals exiting fibers 32 are supplied to a dichroic filter 34, which separates the signals. A first signal ($\lambda_1$) is reflected by the filter and is supplied via fiber 35 to a photodiode 36 which is, in turn, connected to a pre-amp/post-amp 38. The other signal ($\lambda_2$) passes through the dichroic filter 34 and is conveyed via fiber 39 to a photodiode 40 which is, in turn, connected by a pre-amp/post-amp 41. Of course, if there is only one signal of one wavelength (i.e., $\lambda_1$), there is no need for a dichroic filter.

In the illustrated form, the signals are transmitted from the rotor to the stator. However, this arrangement need not invariably obtain. In an alternative arrangement, the signals could be generated on the stator and transmitted to the rotor.

Thus, the improved fiber optic rotary joint 20 broadly includes a VCSEL transmitter 23 which contains a plurality of light sources, as discussed infra. Each light includes a first light source arranged to selectively generate a first optic signal at a first wavelength ($\lambda_1$) and a second light source arranged to selectively generate a second optic signal at a second wavelength ($\lambda_2$). A first plurality of light emitters 25 are spaced equidistantly along the facing surface 26 of the rotor and individually separated by a first arc distance for transmitting optical signals received from the light sources toward the facing surface 29 of the stator. A first plurality of first optical fibers (24A, 24B, 24C, . . . , 24L) severally communicate respective ones of the light sources with respective ones of the light emitters for conveying optical signals from each respective light source to the associated emitter. A second plurality of light receptors, severally indicated at 31, is spaced equidistantly along the facing surface 29 of the stator and individually separated by a second arc distance. At least one light detector (36, 40) is mounted on the other of the rotor and stator. The improved FORJ further includes a second plurality of second optical fibers, severally indicated at 32, severally communicating respective ones of the light receptors with the light detector(s). The light sources, first optic fibers, light emitters, light receptors, second optical fibers and detector(s) are so configured and arranged that the aggregate propagation delay of the optical signal transmitted from the light sources to the detectors is less than about one-quarter of the bit width of the optical signal. The improved FORJs are capable of transmitting the optical signals at high data rates (e.g., on the order of about 2.5 Gbps or greater) across the interface with reduced jitter.

A first form of the VCSEL transmitter is depicted in FIG. 2. In this form, the VCSEL transmitter is indicated at 23A. The VCSEL transmitter is shown as having twelve different light sources spaced about its periphery. The first optical fibers, severally indicated at 24A, 24B, 24C, . . . , are associated with respective ones of the twelve light sources on the VCSEL transmitter. These various light sources are indicated at 42, and severally identified by the letters A, B, C, . . . . The various fibers 24A, 24B, 24C, . . . may have a core diameter of about 200 microns.

FIG. 2A is an enlarged perspective view of light source 42C. This light source is shown as having a first light source 43C arranged to selectively generate a first optical signal at a first wavelength ($\lambda_1$) and second light source 43C' arranged to selectively generate a second optical signal at a second wavelength. In this first arrangement, the two light sources are arranged to generate the same optical signal at the same wavelength ($\lambda_1$). Hence, the legends $\lambda_1$, $\lambda_1$ are depicted alongside the two light sources. The two light sources are mounted on the upper planar horizontal surface of a support adjacent the apex of two convergent surfaces. The two light sources are supported by mounting blocks 44C, 44C'. The two light sources 43C, 43C' are shown as being arranged in close proximity to the entrance end of optical fiber 24C. Each of these light sources is arranged to selectively generate the optical signal. However, under normal circumstances, only one of the light sources (i.e., 43C) is normally arranged to generate the optical signal. The other light source is arranged to generate the same optical signal only if the first light source fails to generate an optical signal. The invention may further include a sensor for determining whether the first light source is generating the optical signal, and a switch arranged to cause the second light source to generate the optical signal if the first light source fails to generate the optical signal. Preferably, this switch operates automatically upon the sensed failure of the optical signal generated by the first light source so that the supply of the optical signal to the associated first optical fiber will be uninterrupted. In other words, the second light source becomes operable upon the failure of the first optical source. That is not to say that there may not be some error in the bit error rate during the transition from one light source to the other. However, the second light source stands as a standby ready to generate the signal in the absence of the signal generated by the first light source. The structure and operation of one of these light sources more fully shown and described in U.S. Pat. No. 7,158,700 B2, the aggregate disclosure which is hereby incorporated by reference.

Referring now to FIGS. 3 and 3A, a second form of the improved VCSEL transmitter is generally indicated at 23B. This transmitter is functionally similar to that shown in FIG. 2 in that it contains some twelve light sources, severally indicated at 42 and individually identified by the suffices A, B, C, . . . , L. Each light source is associated with the entrance end of a fiber, again indicated at 24A, 24B, 24C, . . . , 24L.

FIG. 3A illustrates the structure of one of the light sources. In this case, the light source 42C is shown as having individual light sources 43C, 43C' mounted on the upper planar horizontal surface of mounting blocks 44C, 44C' adjacent the apexes between two convergent surfaces. However, while the light sources physically appear to be the same, they are different. First light source 43C is arranged to generate a first optical signal at a first wavelength $\lambda_1$, and the second light source 43C' is arranged to selectively generate a second optical signal at a second wavelength $\lambda_2$. The position of the two light sources relative to the entrance end of fiber 24C is the same as in FIG. 2A. Thus, whereas FIG. 2A discloses two proximate light sources operatively arranged to generate the same optical signal at the same wavelength (i.e., $\lambda_1$-$\lambda_1$), the arrangement shown in FIG. 3A is arranged to generate two different optical signals at two different wavelengths (i.e., $\lambda_1$-$\lambda_2$). Thus, whereas the arrangement shown in FIG. 2A offers the feature of redundancy, the arrangement shown in FIG. 3A offers the advantage of providing a number of different light sources.

Referring now to FIGS. 4 and 4A yet another embodiment of the VCSEL transmitter is indicated at 23C. This transmitter is shown as having a plurality of light sources, 42A, 42B, 42C, . . . , 42L, associated with first optical fibers 24A, 24B, 24C, . . . , 24L, respectively. However, as best shown in FIG. 4A, the four light sources 43C, 43C', 45C, 45C' are mounted on the planar upper horizontal surfaces of mounting blocks, again severally indicated at 44, adjacent the apexes formed by the converging surfaces. First and second light sources 43C, 43C' are arranged to selectively generate the optical signal of the first wavelength $\lambda_1$. The other two optical sources 45C, 45C' are arranged to generate a different optical signal at the second wavelength $\lambda_2$. This arrangement offers the combined feature of redundancy, and a coupling of two different optical signals. In other words, light source 43C may normally generate the first optical signal at wavelength $\lambda_1$. Light source 43C' is normally in a standby mode and is caused to generate the first light source only upon the sensed failure of light source 43C. Similarly, the second optical signal is normally generated by light source 45C. The fourth light source 45C' is normally in standby mode, and is only caused to generate the second optical signal upon the sensed failure of light source 45C. Thus, this arrangement is a marrying of the redundant features afforded by the first arrangement shown in FIGS. 2A and 2B, and couples two different signals, such as shown in FIGS. 3 and 3A.

As shown in FIG. 4B, the four VCSEL transmitters are arranged at the corners of an imaginary square having a centerline spacing along one of its sides of about 70±2 microns. Accordingly, the diagonally-opposite VCSEL transmitters are spaced from one another by a centerline distance of about 100±2 microns. In FIG. 4B, such diagonally-opposite transmitters are indicated as being spaced by a centerline distance of about 100 microns. FIG. 4B also shows a circle having a diameter of about 200 microns. This represents the core of the fiber, and illustrates how well four VCSEL light sources can fit within the projected area of the core.

Referring now to FIG. 5, an improved FORJ, generally indicated at 50, is shown as including a VSCEL transmitter with a channel selector, again generally indicated at 23, and a rotor 51 mounted for rotation within a stator 52. A plurality of receptors, again severally indicated at 31, communicate the receptors via optical fibers 32 and bundled fibers 30 with receivers, again indicated at 33. In FIG. 5, four 2.5 Gbps electrical signals are supplied from an external data acquisition system ("DAS") to the VSCEL transmitter. The VSCEL transmitter is also provided with a rotor position input, such as from a CPU, a resolver, an encoder, or the like. The four input signals are electrical. The four input signals cause the various light sources 42A, 42B, 42C, . . . to generate light at a first wavelength $\lambda_1$. This light is then supplied to the twelve emitters that are spaced equally about the rotor. Here again, the emitters are indicated at 25A, 25B, 25C, . . . . The optical signal supplied from the VSCEL transmitter to the rotor is indicated as being present in optical fiber bundle 54.

In this arrangement, there are optical pick-ups arranged in each of four quadrants of the stator. Each pick-up is shown as including ten receptors, severally indicated at 31, which communicate via fibers 32 and 30 with receivers 33. The VSCEL transmitter 23 includes a switch for routing each individual input data stream to a respective one of the light sources that communicates with an appropriate emitter 25 that is arranged to transmit a corresponding optical signal to a predetermined light receptor for that particular relative angular position between the rotor and the stator. Thus, each light emitter will transmit an individual optical data signal to the associated light receptor at the relative angular position between the rotor and stator so that the individual optical data signals will be transmitted continuously to respective ones of the light receptors. The received optical signals, again at wavelength $\lambda_1$, are supplied to the four receivers, one being associated with each quadrant, to convert the received optical signals into digital electrical signals. Thus, this first arrangement has receptors in each of the four quadrants, with the DAS supplying four electrical input data streams, each at 2.5 Gbps. The device operates at a single wavelength ($\lambda_1$) by selectively switching the digital signals to those emitters that communicate with the receptors in a particular quadrant so that the individual optical data signals will be transmitted continuously to respective ones of the light receptors. The received signals are then converted back to electrical signals. Since this arrangement operates at a single wavelength, there is no need for a dichroic filter. The maximum output of this system is about 10 Gbps.

Referring now to FIG. 6, a further improved fiber optic rotary joint is generally indicated at 60. This joint is again shown as having a VSCEL transmitter with a channel selector. The VSCEL transmitter includes individual light sources 42A, 42B, 42C, . . . . The VSCEL transmitter is supplied with eight individual electrical data streams, each having a data transmission rate of 2.5 Gbps. The VSCEL transmitter is also provided with a rotor position input signal from a resolver, an encoder, a CPU, or the like. In this arrangement, however, the supplied electrical data signals are converted into digital optical signals of two different wavelengths, $\lambda_1$ and $\lambda_2$. The VSCEL transmitter is arranged to supply the combined optical signal to various ones of the emitters 25A, 25B, . . . , provided on the outer peripheral surface of a rotor 61. These emitters are arranged to emit light tangentially toward various pick-ups arranged in each of four quadrants provided on the stator. Each pick-up is shown as including receptors, severally indicated at 31, that communicate via optical fibers 32 and bundled fibers 30 with a series of receivers 33. The VSCEL transmitter includes a switch for routing each individual input data stream to a respective one of the light sources that communicates with the appropriate emitter that is arranged to transmit a corresponding optical signal to a predetermined light receptor for that particular relative angular position between the rotor and the stator such that each light emitter will transmit an individual optical data signal to such associated light receptor at such relative angular position so that the individual optical data signals will be transmitted continuously to respective ones of the light receptors. Line 64 is shown as containing the two optical signals ($\lambda_1+\lambda_2$), and communicates the various light sources in the VSCEL transmitter with the rotor-mounted emitters. Similarly, after transmission to the receptors, the bundled fibers are also shown as containing the combined signals of both wavelengths, $\lambda_1+\lambda_2$. In this arrangement, the dichroic filter is used to separate the two signals. Thus, each receiver 33 includes a $\lambda_1$ receiver and a $\lambda_2$ receiver. The outputs of each of these are again converted to analog electric signals, each at the originally-supplied 2.5 Gbps data rate. Thus, the arrangement shown in FIG. 6 has receptors in each of four quadrants. This arrangement also has both switching and wave division multiplexing. Hence, the maximum output of this system is on the order of 20 Gbps.

MODIFICATIONS

The present invention contemplates that many changes and modifications may be made. As comparatively illustrated in FIGS. 5 and 6, the improved FORJ may simply include switching, or may include switching and wave division multiplexing. The individual electrical input data streams supplied to the VCSEL transmitter may be of a single wavelength or of multiple wavelengths. The VCSEL transmitter selectively routes each individual data stream to a respective one of the light sources that communicates with an appropriate emitter that is arranged to transmit a corresponding optical signal to a predetermined light receptor for that particular relative angular position between the rotor and stator such that each emitter will transmit an individual optical data signal to the associated light receptor at such relative angular position so that the individual optical data signals will be transmitted continuously to respective ones of the light receptors. The VSCEL transmitter may have twelve light sources. However, this number is not critical, and the transmitter may have a greater or lesser number of light sources. The light sources may be redundant such that if one light source fails, another will stand in its stead to continue transmission. Alternatively, the VSCEL transmitter may be arranged to provide optical signals of two or more wavelengths.

While FIGS. 5 and 6 show light receiving modules in each of four quadrants of the stator, the number of such light-receiving modules may be changed. There may be fewer than four, or more than four, of such light-receiving modules. The transmitted optical signal is broken down into its components, and is converted back to its electrical analog.

Therefore, while several preferred embodiments of the inventive FORJ have been shown and described, and several modifications thereof discussed, persons skilled in this art will readily appreciate that various additional changes and modifications may be made without departing from the spirit of the invention, as defined and differentiated by the following claims.

What is claimed is:

1. A fiber optic rotary joint for enabling the transmission of a substantially-uninterrupted digital optical signal across the interface between facing surfaces of a rotor and a stator, comprising:
   a plurality of light sources mounted on one of said rotor and stator, each light source including a first light source arranged to selectively generate an optical signal and a second light source arranged to selectively generate said optical signal;
   a first plurality of light emitters spaced equidistantly along the surface of said one of said rotor and stator and separated individually by a first arc distance for transmitting said optical signal received from said light sources toward the facing surface of the other of said rotor and stator;
   a first plurality of first optical fibers severally communicating respective ones of said light sources with respective ones of said light emitters for conveying said optical signal from each respective light source to the associated emitter;
   wherein each of said first optical fibers has a core and wherein each of said first and second light sources is operatively arranged to emit said optical signal directly into an end of the associated first optical fiber;
   wherein said first light source is arranged to normally generate said optical signal and wherein said second light source is arranged to generate said optical signal only if said first light source fails to generate said optical signal;
   a second plurality of light receptors spaced equidistantly along the surface of the other of said rotor and stator and separated individually by a second arc distance;
   at least one light detector mounted on the other of said rotor and stator; and
   a second plurality of second optical fibers severally communicating respective ones of said light receptors with said light detector(s);
   said light sources, first optical fibers, light emitters, light receptors, second optical fibers and detector(s) being so configured and arranged that the aggregate propagation delay of the optical signal transmitted from said light sources to said detector(s) is less than about one-quarter of the bit width of said optical signal;
   whereby said fiber optic rotary joint is capable of transmitting said optical signal across said interface with reduced jitter.

2. A fiber optic rotary joint as set forth in claim 1, and further comprising:
   a sensor for sensing whether said first light source is generating said optical signal; and
   a switch arranged to cause said second light source to generate said optical signal if said first light source fails to generate said optical signal.

3. A fiber optic rotary joint as set forth in claim 2 wherein said switch operates automatically upon the sensed absence of said optical signal generated by said first light source.

4. A fiber optic rotary joint as set forth in claim 1 wherein said optical signal is transmitted across said interface at a data transmission rate of at least about 2.5 Gbps.

5. A fiber optic rotary joint as set forth in claim 1 wherein said first and second arc distances are subtended by different angles.

6. A fiber optic rotary joint as set forth in claim 5 wherein said light emitters are separated by an interval of about 30° and said second arc distance is about 36°.

7. A fiber optic rotary joint as set forth in claim 1 wherein said first optical fibers are of substantially equal lengths.

8. A fiber optic rotary joint as set forth in claim 1 wherein said second optical fibers are of substantially equal lengths.

9. A fiber optic rotary joint as set forth in claim 1 wherein the core of each first optical fiber has a diameter of at least about 200 microns.

10. A fiber optic rotary joint as set forth in claim 1 wherein the core of each second optical fiber has a diameter of at least about 200 microns.

11. A fiber optic rotary joint as set forth in claim 1 wherein said first plurality of first optical fibers is different from said second plurality of second optical fibers.

12. A fiber optic rotary joint as set forth in claim 1 wherein said first and second optical fibers are of different lengths.

13. A fiber optic rotary joint as set forth in claim 1 wherein each of said first optical fibers has a collimating lens assembly at a marginal end portion remote from its associated light sources.

14. A fiber optic rotary joint as set forth in claim 1 wherein each of said second optical fibers has a collimating lens assembly at a marginal end portion remote from said light detector(s).

15. A fiber optic rotary joint as set forth in claim 1 wherein the core of each of said first optical fibers is glass.

16. A fiber optic rotary joint as set forth in claim 1 wherein the signal-to-be-transmitted is coupled into various of said first optical fibers prior to transmission across said interface, is optically multiplexed, is transmitted by said plurality of light emitters across said interface, wherein such transmitted signals are received by said second optical fibers, and wherein such received signals are optically demultiplexed to reform said signal.

17. A fiber optic rotary joint as set forth in claim 1 wherein a number of said second plurality of light receptors is spaced about said surface of said other of said rotor and stator.

18. A fiber optic rotary joint for enabling the transmission of substantially-uninterrupted digital optical signals across the interface between facing surfaces of a rotor and a stator, comprising:
   a plurality of light sources mounted on one of said rotor and stator, each light source including two first light sources severally arranged to selectively generate a first optical signal at a first wavelength and two second light sources severally arranged to selectively generate a second optical signal at a second wavelength;
   wherein one of said first light sources is arranged to normally generate said first optical signal, and wherein the other of said first light sources is arranged to generate said first optical signal if said one first light source does not generate said first optical signal;
   a first plurality of light emitters spaced equidistantly along the surface of said one of said rotor and stator and separated individually by a first arc distance for transmitting said optical signals received from said light sources toward the facing surface of the other of said rotor and stator;
   a first plurality of first optical fibers severally communicating respective ones of said light sources with respective ones of said light emitters for conveying said optical signals from each respective light source to the associated emitter;
   wherein each of said first optical fibers has a core and wherein each of said first and second light sources is operatively arranged to emit their respective optical signals directly into an end of the associated first optical fiber;

a second plurality of light receptors spaced equidistantly along the surface of the other of said rotor and stator and separated individually by a second arc distance;

at least one light detector mounted on the other of said rotor and stator; and a second plurality of second optical fibers severally communicating respective ones of said light receptors with said light detector(s);

said light sources, first optical fibers, light emitters, light receptors, second optical fibers and detector(s) being so configured and arranged that the aggregate propagation delay of the optical signals transmitted from said light sources to said detector(s) is less than about one-quarter of the bit width of said optical signals;

whereby said fiber optic rotary joint is capable of transmitting said optical signals across said interface with reduced jitter.

19. A fiber optic rotary joint as set forth in claim 18 wherein said fiber optic rotary joint further includes:

a position determining device for determining the relative angular position between said rotor and stator;

means for supplying a plurality of individual input data streams to said joint; and a switch for routing each individual input data stream to a respective one of said light sources that communicates with the appropriate emitter that is arranged to transmit a corresponding optical signal to a predetermined light receptor for that particular relative angular position between the rotor and stator such that each light emitter will transmit an individual optical data signal to such associated light receptor at such relative angular position so that said individual input data streams will be transmitted continuously to respective ones of said light receptors at any relative angular position between said rotor and said stator.

20. The method of enabling the transmission of a digital optical signal across the interface between facing surfaces of a rotor and a stator, comprising the steps of:

providing a plurality of light sources on one of said rotor and stator, each light source including a first light source arranged to selectively generate an optical signal and a second light source arranged to selectively generate said optical signal;

providing a first plurality of light emitters spaced equidistantly along the surface of said one of said rotor and stator and separated individually by a first arc distance;

providing a first plurality of first optical fibers between respective ones of said light sources and respective ones of said light emitters;

wherein each of said first optical fibers has a core and wherein each of said first and second light sources is operatively arranged to emit the optical signal directly into an end of the associated first optical fiber;

wherein said first light source is arranged to normally generate said optical signal and wherein said second light source is arranged to generate said optical signal only if said first light source fails to generate said optical signal;

causing said light sources to emit said optical signal;

conveying said optical signal from said light sources to said light emitters along said first optical fibers;

causing said first light emitters to transmit said optical signal across said interface toward the facing surface of the other of the rotor and stator;

providing a second plurality of spaced light receptors spaced equidistantly along the surface of the other of said rotor and stator and separated individually by a second arc distance for receiving the optical signals transmitted by said light emitters;

providing at least one light detector on the other of said rotor and stator;

conducting the optical signal received by said light receptors to said light detector(s); and positioning said light emitters and light receptors such that the aggregate propagation delay of the optical signal transmitted between said sources and detector(s) is less than about one-quarter of the bit width of said optical signal;

thereby to enable the transmission of said digital optical signals across said interface with reduced jitter.

21. The method as set forth in claim 20 wherein said first light source is normally arranged to generate said optical signal.

22. The method as set forth in claim 20, and further comprising the additional steps of:

sensing whether said first light source generates said optical signal; and causing said second light source to generate said optical signal if said first light source fails to generate said optical signal.

23. The method as set forth in claim 20, and further comprising the additional steps of:

coupling the signal-to-be-transmitted into each of said first optical fibers prior to transmission across said interface;

multiplexing said signal;

transmitting said signal across said interface;

receiving such transmitted signal; and demultiplexing such received signal to reform said signal.

24. The method of enabling the transmission of digital optical signals across the interface between facing surfaces of a rotor and a stator, comprising the steps of:

providing a plurality of light sources on one of said rotor and stator, each light source including a first light source arranged to selectively generate a first optical signal at a first wavelength and a second light source arranged to selectively generate a second optical signal at a second wavelength;

providing a first plurality of spaced light emitters spaced equidistantly along the surface of said one of said rotor and stator;

providing a first plurality of first optical fibers between respective ones of said light sources and respective ones of said light emitters;

wherein each of said first optical fibers has a core and wherein each of said first and second light sources is operatively arranged to emit their respective optical signals directly into an end of the associated first optical fiber;

causing said light sources to emit said optical signals;

conveying said optical signals from said light sources to said light emitters along said first optical fibers;

causing said first light emitters to transmit said optical signal across said interface toward the facing surface of the other of the rotor and stator;

providing a second plurality of light receptors spaced equidistantly along the surface of the other of said rotor and stator for receiving the optical signals transmitted by said light emitters;

providing at least one light detector on the other of said rotor and stator;

conducting the optical signals received by said light receptors to said light detector(s); and positioning said light emitters and light receptors such that the aggregate propagation delay of the optical signal transmitted between said sources and detector(s) is less than about one-quarter of the bit width of said optical signal;

supplying a plurality of individual input data streams to said joint;

determining the relative angular position between said rotor and stator;

routing each input data stream to the appropriate emitter that transmits a corresponding optical signal to a predetermined light receptor for that determined relative angular position such that each light emitter will transmit an individual optical data signal to such associated light receptor at such relative angular position; and continuously transmitting each of said individual optical data signals to respective ones of said light receptors at any relative angular position of said rotor and stator;

thereby to enable the transmission of said digital optical signals across said interface with reduced jitter.

* * * * *